US00PP35689P3

(12) United States Plant Patent
Martin

(10) Patent No.: US PP35,689 P3
(45) Date of Patent: Mar. 12, 2024

(54) ***CANNABIS* PLANT NAMED 'ZUCHI'**

(50) Latin Name: *Cannabis sativa*
Varietal Denomination: ZUCHI

(71) Applicant: Umami Worldwide, LLC, Las Vegas, NV (US)

(72) Inventor: Chase Martin, Las Vegas, NV (US)

(73) Assignee: UMAMI WORLDWIDE, LLC, Las Vegas, NV (US)

( * ) Notice: Subject to any disclaimer, the term of this patent is extended or adjusted under 35 U.S.C. 154(b) by 0 days.

(21) Appl. No.: 17/950,084

(22) Filed: Sep. 21, 2022

(65) Prior Publication Data

US 2023/0093797 P1 Mar. 23, 2023

Related U.S. Application Data

(60) Provisional application No. 63/247,285, filed on Sep. 22, 2021.

(51) Int. Cl.
*A01H 5/00* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./258, 263.1
CPC ... A01H 5/00; A01H 5/12; A01H 5/02; A01H 6/28
See application file for complete search history.

(56) References Cited

PUBLICATIONS

Seed Finder for Zuchi, retrieved on Apr. 17, 2023 at https://en.seedfinder.eu/strain-info/Zuchi/Umami_Seed_Co/#descendants, 6 pp. (Year: 2023).*

* cited by examiner

*Primary Examiner* — June Hwu
(74) *Attorney, Agent, or Firm* — Leonard R. Svensson; Intelink Law Group, P.C.

(57) ABSTRACT

The *Cannabis* cultivar 'Zuchi' can be briefly characterized by having a zigzag stem structure, medium length petioles, short internodal stacking, triangle-shaped flowers, and bulky flowers with little to no stem. It produces large towering colas up to 2' in uninterrupted length. It has a short flowering time of less than 70 days, usually 60-65 days. Female plants having 'Zuchi' as the male parent generally have deep purple and blue colorations in 50-75% of the progeny that are high yielding, greater than 50 grams/ft$^2$ under optimal conditions.

6 Drawing Sheets

Latin name of the genus and species: *Cannabis sativa.*
Variety denomination: 'ZUCHI'.

BACKGROUND OF THE INVENTION

This invention relates to a new and distinctive male *Cannabis* cultivar designated as 'ZUCHI'.

TAXONOMY AND NOMENCLATURE

*Cannabis*, more commonly known as marijuana, is a genus of flowering plants that includes at least three species, *Cannabis sativa, Cannabis indica*, and *Cannabis ruderalis* as determined by plant phenotypes and secondary metabolite profiles. In practice however, *Cannabis* nomenclature is often used incorrectly or interchangeably. *Cannabis* literature can be found referring to all *Cannabis* varieties as "*sativas*" or all cannabinoid producing plants as "*indicas*". Indeed, the promiscuous crosses of indoor *Cannabis* breeding programs have made it difficult to distinguish varieties, with most *Cannabis* being sold in the United States having features of both *sativa* and *indica* species.

Human cultivation history of *Cannabis* dates back 8000 years (Schultes, R E., 1970, Random thoughts and queries on the botany of *Cannabis*. Pages 11-38 in: CRB Joyce, and S H Curry eds., THE BOTANY AND CHEMISTRY OF

*CANNABIS*. J. & A. Churchill. London, England). Hemp cloth recovered in Europe dates back 6000 years (Small, E, Beckstead, H D, and Chan, A, 1975, The evolution of cannabinoid phenotypes in *Cannabis*, ECONOMIC BOTANY 29(3):219-232). The written record of the pharmacologic properties of *Cannabis* goes back more than 4000 years (Ti, H. 2737 BC. NEI JING SU WEN HUANG TI, Yellow Emperor's Classic on Internal Medicine; referred to without citation in Small et al. 1975 Supra).

The taxonomy and nomenclature of the highly variable genus *Cannabis* (Emboden, W A, 1974, ECONOMIC BOTANY 28(3):304-310; Small, E and Cronquist, A, 1976, TAXON 25(4):405-435; Small E and Cronquist, A, 1977, TAXON 26(1):110; Hillig, K W and Mahlberg, P G, 2004, American Journal of Botany 91(6):966-975), remains in question. This is in spite of the fact that its formal scientific name, *Cannabis sativa* L., assigned by Carolus Linneaus (Linnaeus, C, 1753, SPECIES PLANTARUM, 2:1027, Salvius, Stockholm, Facsimile edition, 1957-1959, Ray Society, London, U.K.), is one of the oldest established names in botanical history and is still accepted to this day. Another species in the genus, *Cannabis indica* Lam. was formally named somewhat later (de Lamarck, J B, 1785, ENCYCLOPEDIE METHODIQUE DE BOTANIQUE, 1(2):694-695), but is still very old in botanical history. In 1785, Jean-Baptiste Lamarck published a description of a second species of *Cannabis*, which he named *Cannabis indica*. Lamarck based his description of the newly named species on plant specimens collected in India. *C. indica* was described as relatively short, conical, and densely branched, whereas *C. sativa* was described as tall and laxly branched (Schultes R. E. et al, 1974, Harvard University Botanical Museum Leaflets, 23:337-367). *C. indica* plants were also described as having short, broad leaflets whereas those of *C. sativa* were characterized as relatively long and narrow (Anderson L. 1980, Harvard University Botanical Museum Leaflets, 28:61-69). *C. indica* plants conforming to Schultes' and Anderson's descriptions may have originated from the Hindu Kush mountain range. Because of the often harsh and variable (extremely cold winters, and warm summers) climate of those parts, *C. indica* is well-suited for cultivation in temperate climates.

Three other species names were proposed in the 1800s to distinguish plants with presumably different characteristics (*C. macrosperma* Stokes, *C. chinensis* Delile, *C. gigantean* Vilmorin), none of which are accepted today, although the epithet "*indica*" lives on as a subspecies of *C. sativa* (*C. sativa* ssp. *indica* Lam., Small and Cronquist 1976 Supra).

In the 20th century, two new names were added to the 50 liturgy of proposed *Cannabis* species: *C. ruderalis* Janischevsky and a hybrid, x *C. intersita* Sojak. (Small, E, Jui, P Y, and Lefkovitch, L P, 1976, SYSTEMATIC BOTANY 1(1): 67-84; Small and Cronquist 1976 Supra). Further, numerous names have been proposed for horticultural variants of *Cannabis* but as of 1976, "very few of these have been validly published as formal taxa under the International Code of Botanical Nomenclature" (Small and Cronquist 1976 Supra). Moreover, other recent work continues to focus on higher-order evolutionary relationships of the genus. *Cannabis* has been variously ascribed as belonging to mulberry family (Moraceae) (Engler, H G A, Ulmaceae, Moraceae and Urticaceae, pages 59-118 in: A. Engler and K. Prantl eds., 1889, DIE NATURLICHEN PFLANZENFAMILIEN 3(1). W. Engelmann, Leipzig, Germany; Judd, W S, Sanders, R W, and Donoghue, M J, 1994, HARVARD PAPERS IN BOTANY 5:1-51; Humphries, C J and Blackmore, S, A review of the classification of the Moraceae, pages 267-277 In: Crane and Blackmore 1989 id.); nettle family (Urticaceae) (Berg, C C, Systematics and phylogeny of the Urticales, pages 193-220, in: P. R. Crane and S. Blackmore eds., 1989, EVOLUTION, SYSTEMATIC, AND FOSSIL HISTORY OF THE HAMAMELIDAE, VOL. 2, HIGHER HAMAMELIDAE, Clarendon Press, Oxford, U.K.); and most recently in its own family with hops (Humulus), Cannabaceae, or hemp family (Sytsma, K J, et al, 2002, AMERICAN JOURNAL OF BOTANY 89(9): 1531-1546). While the work of Small and Cronquist 1976 Supra, seemed to effectively confine the genus to a single species with 2 subspecies (*C. sativa s., C. s. indica*), each with two varieties (*C. s. s.* var. *sativa, C. s. s.* var. *spontanea; C. s. i.* var. *indica, C. s. i.* var. *Kafiristanica*) largely on the basis of chemotaxonomy and interfertility of all forms, more recent work (Sytsma et al. 2002 Supra), proposes a two species concept, resurrecting the binomial *C. indica* Lam. Since Sytsma et al. (2002) provides no key for discriminating between the species, the dichotomous key of Small and Cronquist (1976), which accounts for all forms in nature, whether wild or domesticated, is preferred to classify the characteristics of the plant.

BRIEF DESCRIPTION OF THE INVENTION

The present invention relates to a new and distinct *Cannabis* cultivar designated 'ZUCHI'.

'ZUCHI' is characterized as being a male hybrid cultivar, discovered in Orange County, California, having the following characteristics:

- zig zag stem growth structure (FIGS. 2 and 4)
- little to no purple coloration on the stem unless stressed. If stressed due to improper environment, feed, lighting etc., purple streaking in the stem and at the base of the petiole (FIG. 5) can be observed
- Lemon pine cleaner scent on the stem rub
- short internodal spacing—usually 1 inch or less between nodes
- wavy leaf structure with rounded edge leaf serrations (FIGS. 1, 3, 6, 7, 9)
- Usually a 5 finger leaf set up to 7 at maximum health, 4.5-5" average length The central leaflet is very broad, and each leaf overlaps the others and does not allow light to penetrate.

The central leaflet can be 5-7" long and have a total width of 3"6".

The leaf is lime green with heavy gloss and shines bright in the sun or under HID or LED lighting.

The leaf ridges are very deep and wavy, the leaves do not lie flat but are shaped like a soundwave with equal parts up and down.

The trichomes are mostly tall capitate stalked and are wet and gritty/sandy to the touch, releasing a heavy aroma of dish soap, freshly baked croissants, powder laundry detergent and dryer sheets.

The average number of leaflets is between many, 5-9 depending on the total plant size and health.

The upper leaf surface is lime green PMS 802-802x with the lower surface a light green with lime green PMS 360 with little purple PMS 269 streaking along the stem.

- Petiole length 2-2.5". Petioles are medium, typically 1-4" long and 0.2-0.4" in diameter. The longer and older petioles will not show any anthocyanin production and will stay bright/light green PMS 360. Trichomes are glandular with capitate stalked visible and bulbous trichomes and capitate-sessile trichomes are present all around. Petioles are medium to dark green PMS 349-340 with a light anthocyanin streaking PMS 2738 towards the end of the flowering cycle.
- A darker green leaf PMS 3308 (FIGS. 1, 5, 7) requiring high nitrogen feed when vegetative. We use calcium nitrate as 25% of the vegetative feed formula.
- Vigorous growth—up to several inches per week
- Significant lateral branching. The structure is in between a bush and a pine tree shape (FIG. 2).
- Fast rooting. When cloned, roots appear in 7-10 days on average.
- The plant stretches at 1.5-2× its vegetative size during flowering
- The pollen falls at 20-22 days after flowering
- 45 day flowering total
- No purple coloration on the male plant at any time
- No signs of pre flowering in during vegetative growth regardless of light schedule No signs of intersex traits observed Can be grown under a wide range of conditions, for example using an 18 h light/6 h dark schedule up to constant light Prefers nutrients at 2.7-3.0 EC and a light point measurement of light intensity (PPFD) at 300-500 during vegetative growth and 700-1000 in bloom The *Cannabis* cultivar 'Zuchi' is a male plant that can be briefly characterized by having a zigzag stem structure, medium length petioles, short internodal stacking, triangle-shaped flowers, and bulky flowers with little to no stem. It produces large towering colas up to 2' in uninterrupted length. It has a short flowering time of less than 70 days, usually 60-65 days. Female plants having 'Zuchi' as the male parent generally have deep purple and blue colorations in 50-75% of the progeny that are high yielding, greater than 50 grams/ft$^2$ under optimal conditions.

DETAILED BOTANICAL DESCRIPTION

Figure 1:
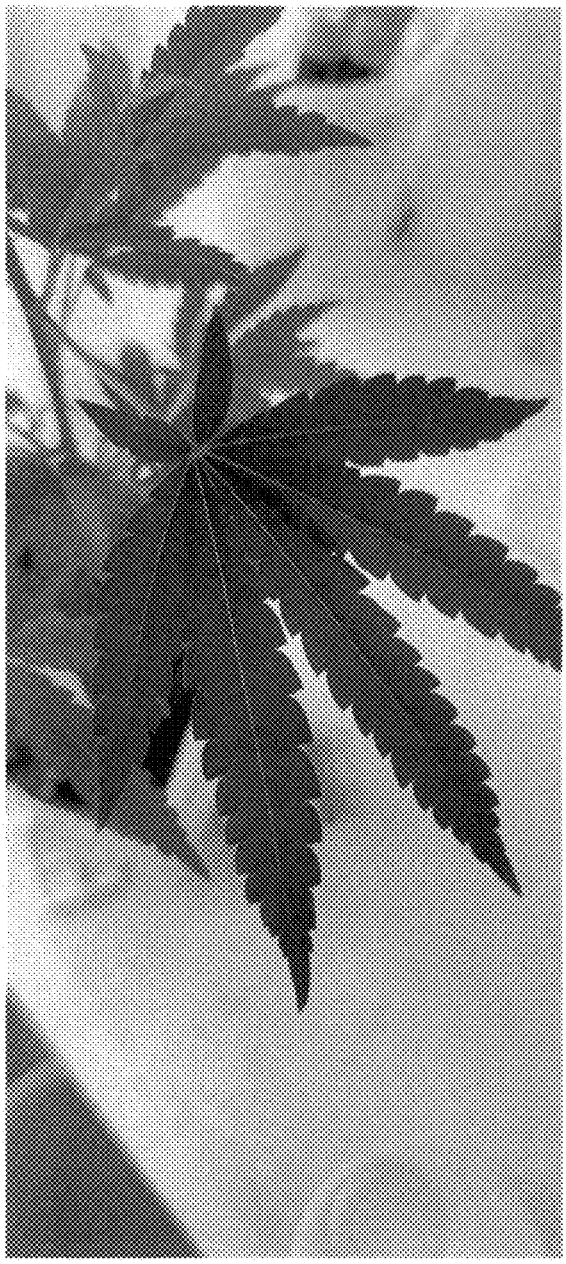
FIG. 1 is a view of the front of a leaf on a 'ZUCHI' plant.
Figure 2:
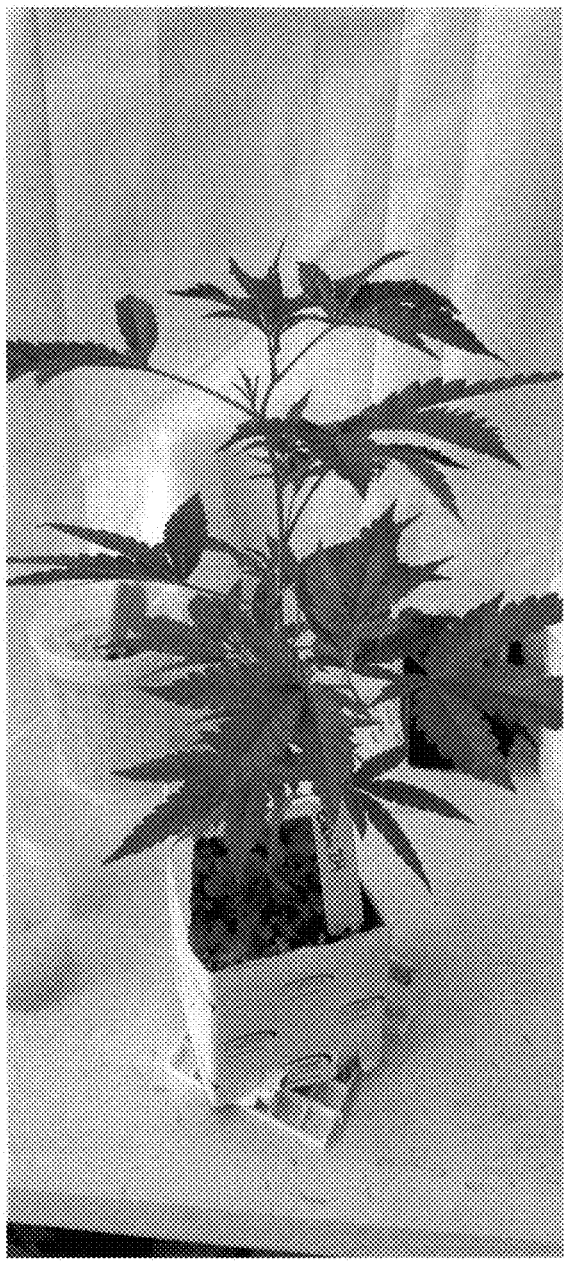
FIG. 2 is a view of a growing 'ZUCHI' plant.
Figure 3:
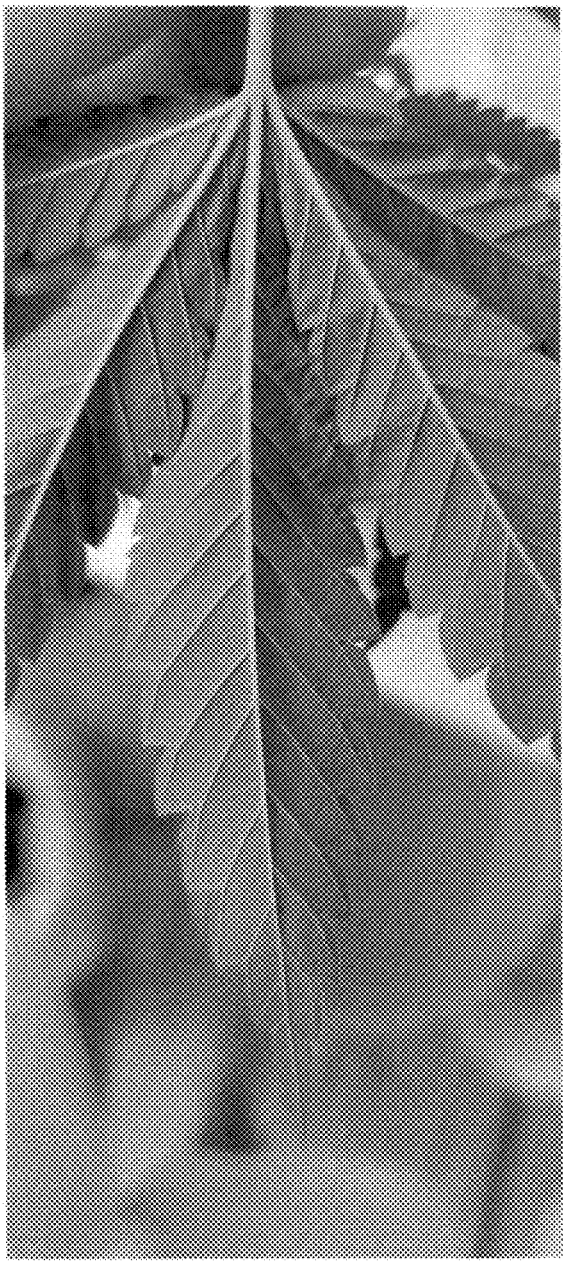
FIG. 3 is a view of the back of a leaf from a 'ZUCHI' plant.
Figure 4:
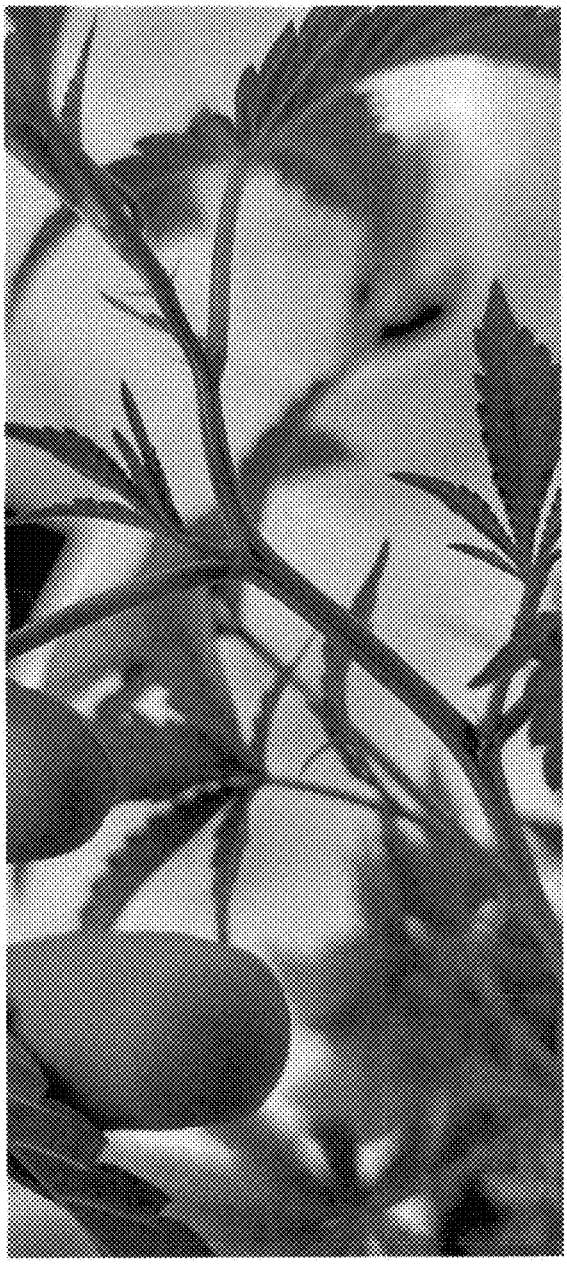
FIG. 4 is a view of the stem of a 'ZUCHI' plant.
Figures 5, 6:
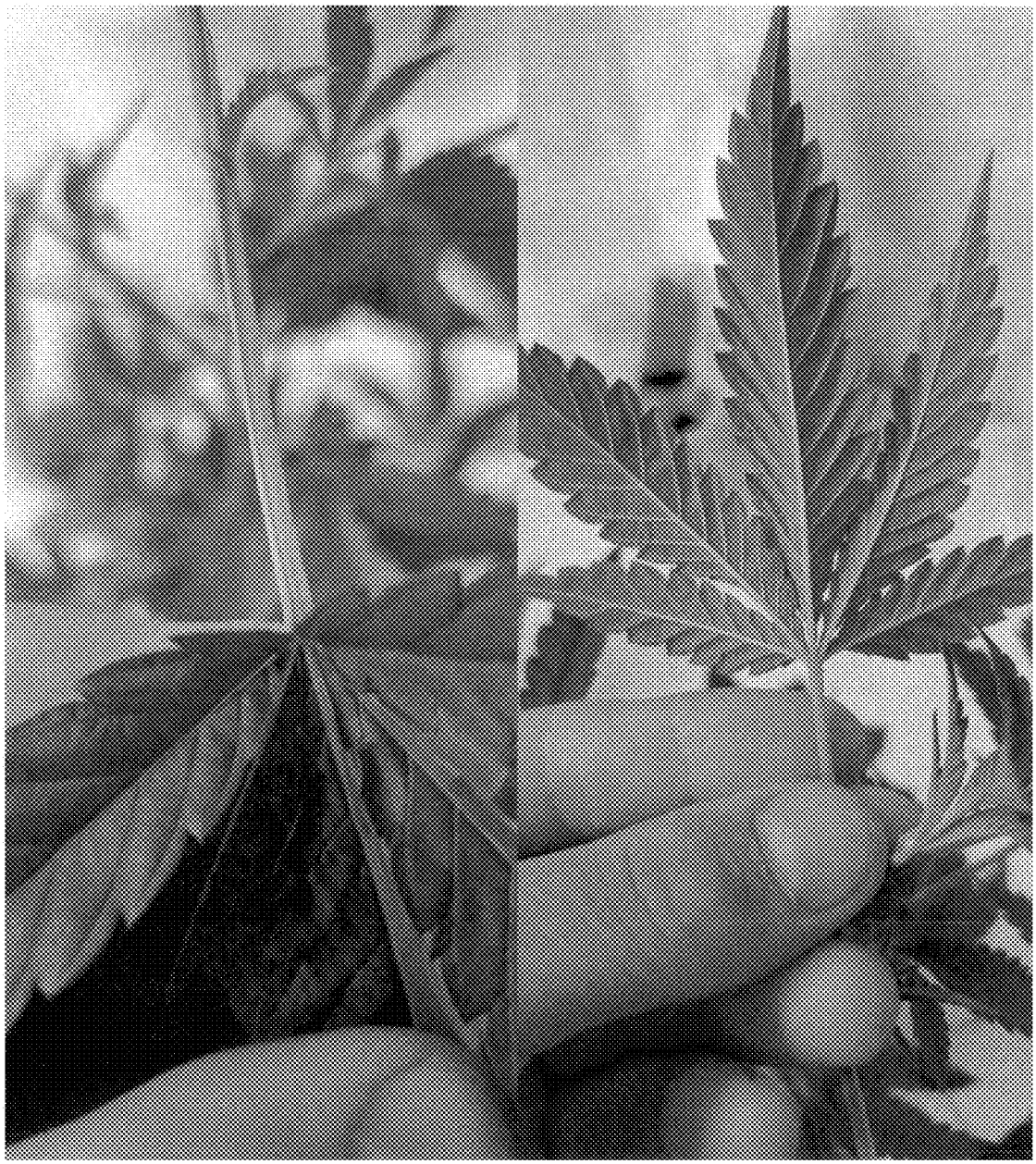
FIG. 5 is a view of a petiole of a 'ZUCHI' plant.
FIG. 6 is a view of the back of a leaf from a 'ZUCHI' plant.
Figure 7:
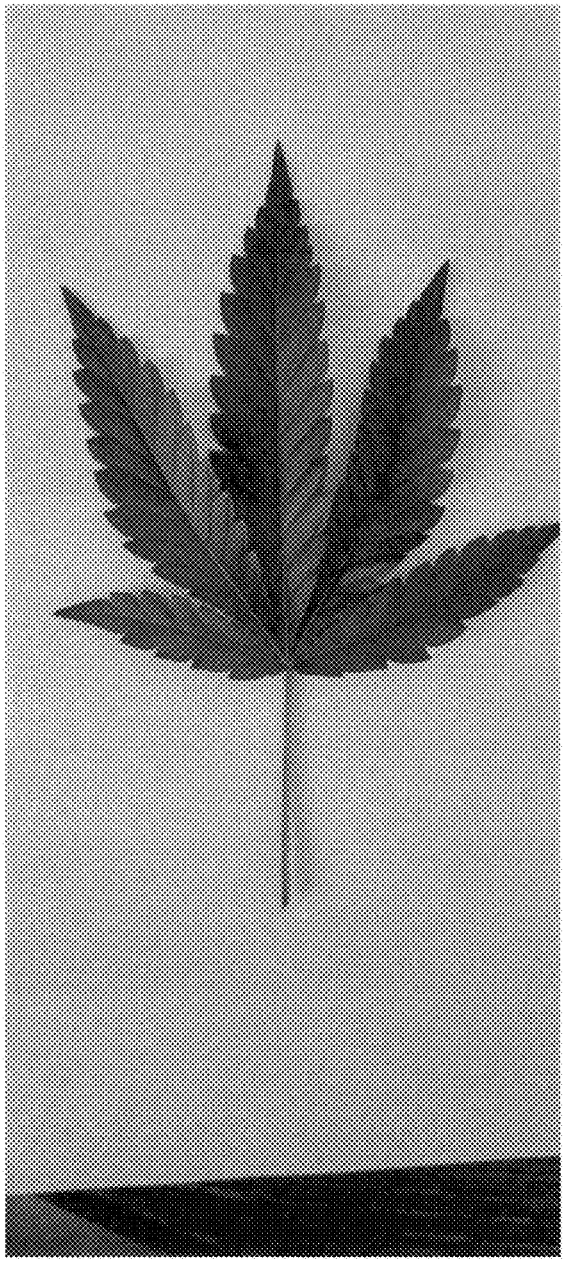
FIG. 7 is a view of the front of a leaf on a 'ZUCHI' plant.
Figure 8:
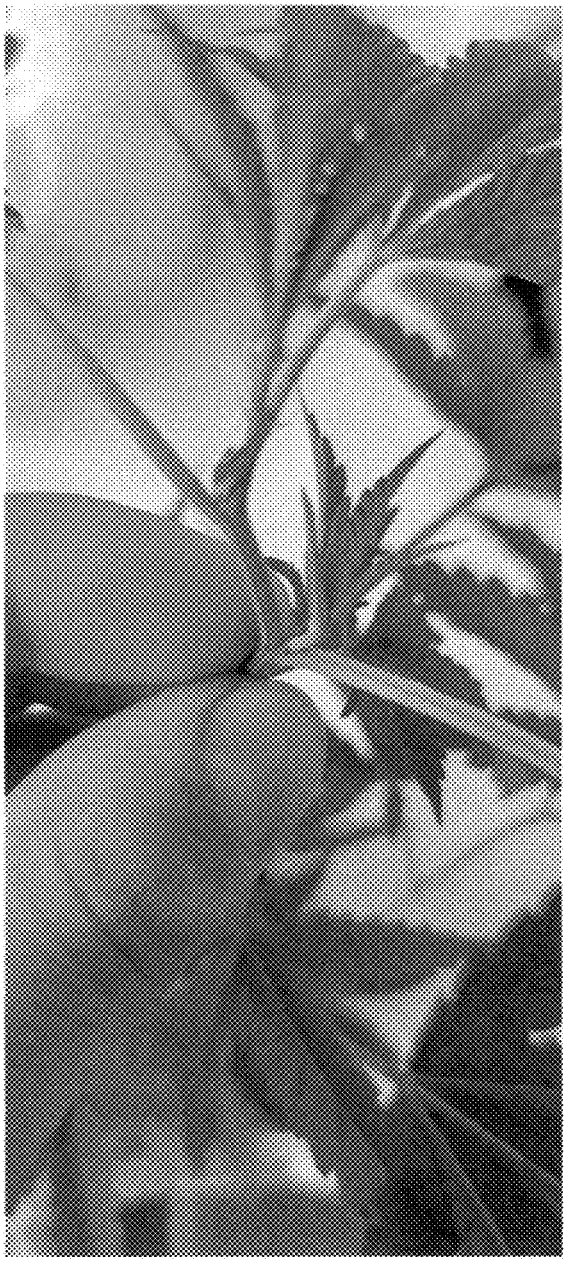
FIG. 8 is a view of the stem of a 'ZUCHI' plant.
Figure 9:
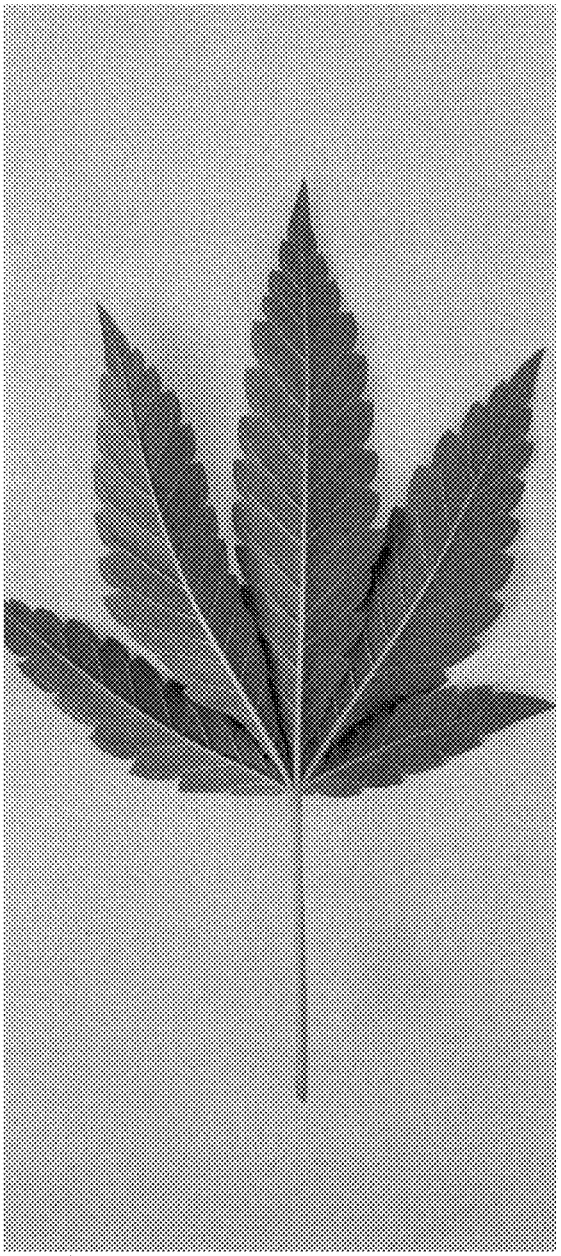
FIG. 9 is a view of the back of a leaf from a 'ZUCHI' plant.
Figure 10:
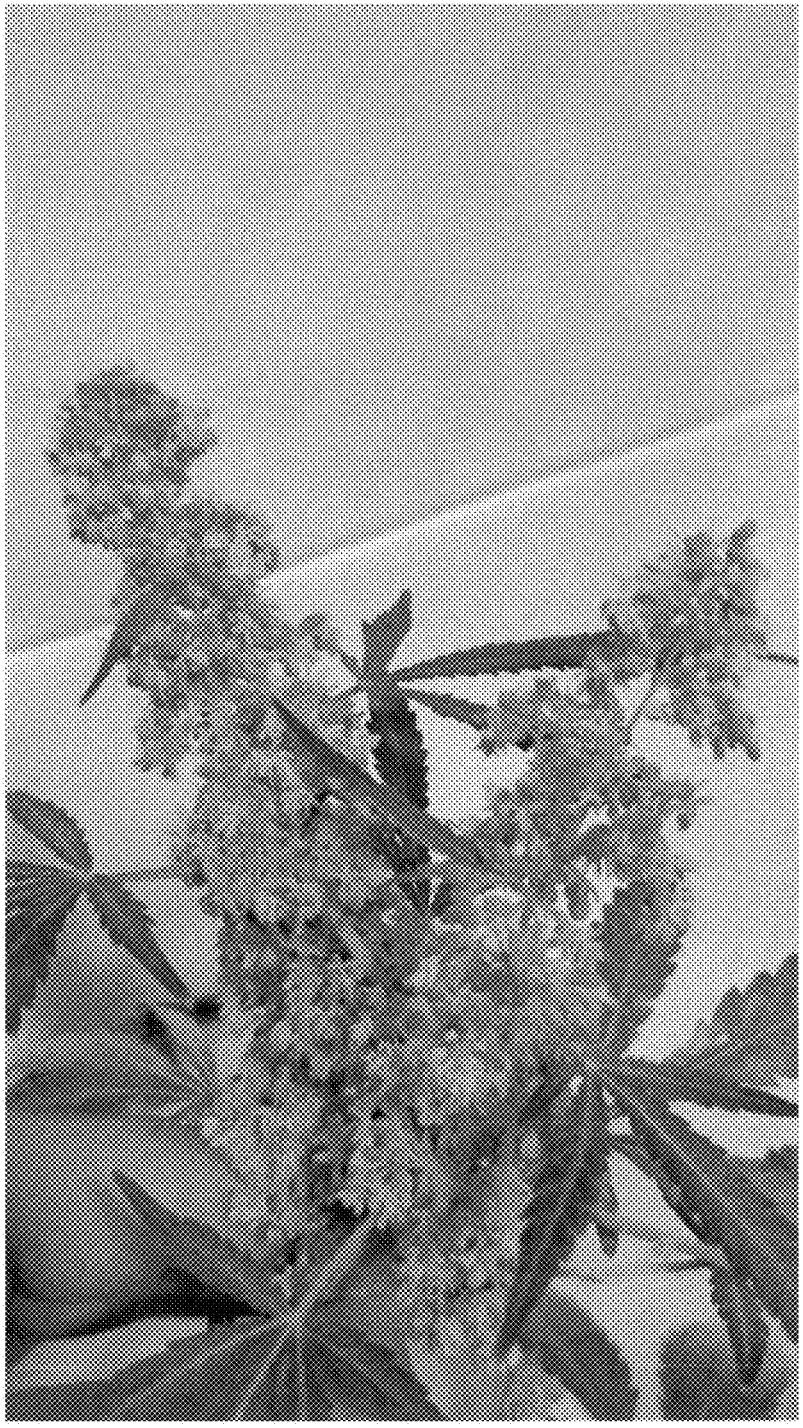
FIG. 10 is a view of a flowering 'ZUCHI' plant.

'ZUCHI' has not been observed under all possible environmental conditions, and the phenotype may vary significantly with variations in environment. The following observations, measurements, and comparisons describe this plant as grown at Mentone, Calif., when grown in the greenhouse, nursery or field, unless otherwise noted.

The color chart referenced is standard hexadecimal Web Pantone Color Chart well known to those of ordinary skill in Internet web site design.

The plant:

*Type* (*life form and habit*).—Herbaceous tap-rooted annual.

*Classification*.—Cultivars of *Cannabis sativa*, possessing traits of the Subspecies *C. sativa* ssp. *indica* (Lam.). This cultivated line possesses intoxicating properties, and so the Subspecies sativa and its varieties (var. *sativa* and *spontanea*) are eliminated from consideration. Within the next couplet distinguishing within the Subspecies *indica*, fruits are required to separate between the varieties (var. *indica* and var. *kafiris tanica*). No fruits were found on any of the individuals observed, and so discrimination between the varieties is impossible with this key. Nevertheless, cross-section of the stem revealed that the stem can be hollow depending on the supplemental level of monosilicic acid, a characteristic known to occur with the fiber-producing strains of *C. sativa* ssp. *sativa*, and thought to be absent from the intoxicating taxa in the genus. As such, these plants appear to be hybrids of the two subspecies of *Cannabis sativa*, e.g., *C. sativa sativa* and *C. sativa indica*.

Origin, form, and growth characteristics:

*Origin*.—Whole Plant pollination of a proprietary male cultivar created by the inventor and the female plant Z. 'Zuchi' is a hybrid cultivar discovered in Orange County California, U.S. It is the first generation from that hybrid line. 'Zuchi' is different from the parent cultivars in terms of its 25-30% increase in size, flower yield, and distinguished from its parents and related known cultivars (such as co-pending plant patent applications for 'AFZ' (Ser. No. 17/950,086) and 'TZT' (Ser. No. 17/950,089) with unique spiced soap flavor and smell profile. The time to clone was reduced by over 20% and the pollen is so potent that it can drastically improve any pollen donor.

*Propagation*.—The strain is perpetuated solely by tissue culture, cloning and cuttings. The new plant reproduces true to type with all of the characteristics, as herein described, firmly fixed and retained through successive generations of such asexual propagation in Orange County, California.

*Mature habit*.—Tap-rooted annual, with an extensive fibrous root system, upright and lateral branched aerial portion of the plant. The growth form of all cloned individuals seen (n=10) was highly manipulated by the systematic removal of terminal buds, inducing a greater branching habit. The cannabinoids and terpene analysis are from the dry female flower of the same phenotype. The method used was High-performance liquid and gas chromatography, otherwise known as HPLC and GCMS. The standard analytical method for these compounds. No analytical data from the described asexually reproduced plant is available. Overall size in this form varies in the population from 1-2 m tall and 0.5-1 m across at their widest point. Many petiole and scars on stems from systematic removal of large shade leaves. In this habit, these are very vigorous annual herbs.

*Growth*.—Very vigorous annuals herbs. Foliage. Leaves.

*Arrangement*.—Alternate, with a zig zag structure.

*Form*.—Palmately compound, (3) 5-7 (9) linear-lanceolate leaflets with glandular hairs.

*Size*.—Remaining (those still present when plants were observed) shade leaves, whole. Shade leaf also known as Fan leaves, are the large leaf connected to the main stem.

*Leaf* (*with petiole*).—8-10" long; middle (largest) leaflet 5-6 inches long, 1.25-2" wide. Shade leaf also known as Fan leaves, are the large leaf connected to the main stem.

*Margins*.—Coarsely serrate.

*Leaf color*.—Top — dark green, PMS 355-357.

*Leaf color*.—Bottom — light green, PMS 359.

*Veins, bottom*.—Pronounced midrib, with straight axial branches at about 45° angle, toward distal end of leaflet.

*Color of bottom veins*.—Light green, PMS 802-802x.

*Petiole*.—Length: 2-2.5" at maturity. Color. Light green, PMS 359.

*Stipules*.—3/16" in length and light emerald, green in color PMS 361.

*Aroma*.—Strongly piquant, with hints of limonene (a cyclic terpene also found in Pinus ponderosa).

*Stem*.—Non-hollow, large, rugose, ribbed, with ribs running parallel to stem, 0.5-2" diameter at base when mature. When stressed red PMS 2395 and purple PMS 2685 steaking can occur. The stem shape is a large, edged oval/octogon that has an aggressive zig-zag pattern as it grows. The node angles are up to 45 degrees where each node will begin to grow in the opposite direction of the previous node at the same growth angle. The internodal spacing is very short and compact. The stem is round and can reach a diameter of 1.5-2.0" when grown with a shallow groove depth and thick pith presence (full stems). There are capitate and bulbous visible trichomes growing on the stem.

*Color*.—Light green PMS 361.

*Bottom of stem color*.—Light green, PMS 802-802x. A few eglandular branched hairs.

*Height*.—1.5-1.9 m at anthesis following heavy pruning regime in cultivation.

*Inflorescence*.—

*Blooming habit*.—Elongated thryse, forming large clusters from 0.2-0.5 m in length, densely packed with individual small male calyx subtended by small leaves, these with some observable glandular trichomes.

*Flowers*.—Corolla: petals and calyx unified and collectively appressed to and surrounding the ovary. The flowers are large (4-6" in length and 2" in diameter) and covered in green and yellow pollen sacs. Pollen is released around day 21-23 of the flowering cycle. The stem and pollen sacs have visible and large glandular trichomes with minor purple streaking down the center of each pollen bract.

*Color*.—Light green PMS 359 and yellow PMS 380.

*Diameter*.—Individual flowers 1-3 mm, cyme 5-7 cm diameter and 5 sepals per flower, 4-5 mm in length.

*Shape*.—Urceolate (urn-shaped).

*Calyces*.—Clusters of male calyx flowers can be observed on all stems and branches during flowering Color: Green PMS 364.

*Filaments*.—Filaments are 0.5-1 mm in length.

*Stigma*.—No stigma observed

*Fruit*.—An achene in this genus; however, no fruits were seen.

*Pollen*.—Pollen drops from male calyx flowers during the 3rd to 4th week of flowering.

*Color*.—Pollen is yellow in color PMS 380.

*Stamen*.—Too many to count. Hundreds per flower cluster.

*Petalage*.—The plant is essentially without petals (apetalous); these fused and appressed to the base of the ovary with the calyx as the perianth.

*Flowers*.—Pedicel. Male calyx is connected to the pedicel that is in turn connected to the peduncle that is in turn connected to the main stem.

*Color*.—The flowers are yellowish green and light green in color PMS 368-369.

General characteristics and culture:

*Blooming period*.—Cuttings after rooting will bloom in 3-6 weeks when <12 hrs light applied to induce flowering.

*Hardiness*.—Hardiness in nature unknown as this plant has only been cultivated in controlled conditions. Disease and pest resistance/susceptibility were not observed.

*Breaking action*.—Stems are fibrous, strong, and flexible; highly resistant to breakage. Rooting. >95% success rate with cuttings using Dip 'n Grow® rooting hormone.

*Growth regulator*.—Only naturally occurring cytokines and auxins are used in cultivation. These are derived from kelp, seaweed, and alfalfa extracts. 1-Triacontanol is also used as a biostimulant and is naturally derived from beeswax.

*Market*.—Use for this product is to breed new medical and recreational *Cannabis* plants intended for commercial cultivation of flowers as well as extracts and the creation of infused goods.

*Climate zones*.—The plants are grown and are meant to be grown in a tightly controlled environment. They have been able to withstand temperatures above 105 degrees F. with 95% RH, as well as an RH of as low as 20%. Recent testing has shown that 'Zuchi' is capable of thriving in a greenhouse with temperatures as low as 40 F with 85-95% RH.

*Shipping tolerance*.—Not applicable. This plant has never been shipped and is not intended for live shipment.

All references cited in this specification, including but not limited to patent publications and non-patent literature, and references cited therein, are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A new and distinct variety of *Cannabis* plant named 'Zuchi', substantially as illustrated and described herein.

* * * * *